US009733230B2

(12) United States Patent
Von Herzen et al.

(10) Patent No.: US 9,733,230 B2
(45) Date of Patent: *Aug. 15, 2017

(54) MULTI-MODAL FLUID CONDITION SENSOR PLATFORM AND SYSTEM THEREFOR (71) Applicant: MASTINC, New York, NY (US)

(72) Inventors: Brian Von Herzen, Minden, NV (US); Steven Van Fleet, Lagrangeville, NY (US)

(73) Assignee: MASTINC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/554,414

(22) Filed: Nov. 26, 2014

(65) Prior Publication Data

US 2015/0082872 A1   Mar. 26, 2015

Related U.S. Application Data (63) Continuation of application No. 13/731,659, filed on Dec. 31, 2012, now Pat. No. 8,924,166, which is a
(Continued)

(51) Int. Cl.
*G01N 33/30* (2006.01)
*G01N 33/28* (2006.01)
*B01D 35/143* (2006.01)

(52) U.S. Cl.
CPC ......... *G01N 33/30* (2013.01); *G01N 33/2888* (2013.01); *B01D 35/143* (2013.01); *B01D 2201/54* (2013.01)

(58) Field of Classification Search
CPC .... G01M 15/042; G01M 15/05; F01M 11/10; F16N 2250/00; F16N 2270/50; G01N 33/2888; G01N 27/02
(Continued)

(56) References Cited

U.S. PATENT DOCUMENTS 5,105,372 A * 4/1992 Provost .................... G07C 3/00
                                                        324/378
5,384,535 A * 1/1995 Mayeur .................. B03C 1/282
                                                        324/204
(Continued)

FOREIGN PATENT DOCUMENTS

DE    10 2004 032 538         1/2006
DE       102004032538 A1 *   1/2006  ............. F02D 41/20
(Continued)

OTHER PUBLICATIONS

Non-Final Office Action in co-pending U.S. Appl. No. 13/621,599 mailed Oct. 3, 2013.
(Continued)

*Primary Examiner* — Carol S Tsai
(74) *Attorney, Agent, or Firm* — Seyfarth Shaw LLP (57) ABSTRACT This invention encompasses embodiments for multi-modal integrated simultaneous measurement of various aspects of fluids contained in circulating systems such as automotive reciprocating engines and vehicle transmissions. These circulating systems perform constant internal lubrication, and heat and contaminant removal to protect the internal moving parts from the inherent friction and damage in normal operation. Most commonly this is achieved with fluids based on hydrocarbon and/or related synthetics, which, over time, can lose their protective properties, and vary in their performance or breakdown/decay due to internal and external events. Several components within the lubricant fluid can be measured and can provide insight into the efficacy of the system to perform its designed mission. Described herein is a real-time, simultaneous, integrated, multi-modal sensor system for early warning notification that can be further enhanced using specifically designed nanoparticles that can be introduced into the system, engineered to specifically bind with the contaminants and/or undergo an irreversible
(Continued)

state change upon certain experienced conditions to both increase the detectability as well as provide for a framework to improve filter performance.

19 Claims, 6 Drawing Sheets

Related U.S. Application Data continuation of application No. 13/621,599, filed on Sep. 17, 2012, now Pat. No. 9,020,766.

(60) Provisional application No. 61/538,282, filed on Sep. 23, 2011.

(58) Field of Classification Search
USPC ...... 702/50; 210/85, 86, 87; 192/101, 103 C
See application file for complete search history.

(56) References Cited

U.S. PATENT DOCUMENTS

| | | | | |
|---|---|---|---|---|
| 6,298,834 | B1 * | 10/2001 | Thead | F02M 31/18 123/549 |
| 6,868,325 | B2 * | 3/2005 | Menon | F02C 9/00 701/100 |
| 7,442,291 | B1 * | 10/2008 | Discenzo | B01D 35/143 210/443 |
| 7,695,300 | B2 * | 4/2010 | Leccia | H01H 9/02 439/263 |
| 8,643,388 | B2 * | 2/2014 | Hedges | G01N 33/2888 324/698 |
| 2003/0102050 | A1 * | 6/2003 | Matthews | F01M 11/04 141/65 |
| 2010/0294231 | A1 * | 11/2010 | Kusel | F01M 1/12 123/196 R |
| 2012/0186445 | A1 * | 7/2012 | Geissler | F01B 31/12 92/5 R |

FOREIGN PATENT DOCUMENTS

| | | | | |
|---|---|---|---|---|
| DE | WO 2010133272 | A2 * | 11/2010 | ............. G01D 21/00 |
| FR | WO 2009106711 | A2 * | 9/2009 | ......... G01N 29/0645 |
| WO | WO 2009/106711 | | 9/2009 | |
| WO | WO 2010/133272 | | 11/2010 | |

OTHER PUBLICATIONS

Non-Final Office Action in co-pending U.S. Appl. No. 13/621,599 mailed Jul. 7, 2014.
Notice of Allowance in co-pending U.S. Appl. No. 13/621,599 mailed Oct. 15, 2014.
Non-Final Office Action in co-pending U.S. Appl. No. 13/731,659 mailed Oct. 3, 2013.
Non-Final Office Action in co-pending U.S. Appl. No. 13/731,659 mailed Jun. 30, 2014.
Notice of Allowance in co-pending U.S. Appl. No. 13/731,659 mailed Oct. 26, 2014.
Non-Final Office Action in co-pending U.S. Appl. No. 13/731,647 mailed Oct. 9, 2014.
Restriction Requirement in co-pending U.S. Appl. No. 13/844,139 mailed Nov. 28, 2014.
Non-Final Office Action in co-pending U.S. Appl. No. 13/840,452 mailed Feb. 12, 2015.
Non-Final Office Action in co-pending U.S. Appl. No. 13/844,139.
Final Office Action in co-pending U.S. Appl. No. 13/731,647 mailed Apr. 17, 2015.
Final Office Action in U.S. Appl. No. 13/844,139, mailed Sep. 10, 2015.
Non-Final Office Action in U.S. Appl. No. 14/523,526, mailed Sep. 18, 2015.
Notice of Allowance in U.S. Appl. No. 13/844,139, mailed Mar. 11, 2016.

* cited by examiner

MULTI-MODAL FLUID CONDITION SENSOR PLATFORM AND SYSTEM THEREFOR

This application is a continuation application of U.S. application Ser. No. 13/731,659, which was flied Dec. 31, 2012, and has been allowed, which is a continuation application of U.S. Ser. No. 13/621,599, which was filed Sep. 17, 2012, and has been allowed and claims the benefit of U.S. provisional patent application No. 61/538,282, which was filed Sep. 23, 2011, the disclosures of each of which is incorporated herein by reference in their entireties.

FIELD OF THE INVENTION

This invention encompasses embodiments for multimodal integrated simultaneous measurement of various aspects of fluids contained in circulating systems such as automotive reciprocating engines and vehicle transmissions. These circulating systems perform constant internal lubrication, and heat and contaminant removal to protect the internal moving parts from the inherent friction and damage in normal operation. Most commonly this is achieved with fluids based on hydrocarbon and/or related synthetics, which, over time, can lose their protective properties, and vary in their performance or breakdown/decay due to internal and external events. Several components within the lubricant fluid can be measured and can provide insight into the efficacy of the system to perform its designed mission. Described herein is a real-time, simultaneous, integrated, multi-modal sensor system for early warning notification that can be further enhanced using specifically designed nanoparticles that can be introduced into the system, engineered to specifically bind with the contaminants and/or undergo an irreversible state change upon certain experienced conditions to both increase the detectability as well as provide for a framework to improve filter performance.

BACKGROUND OF THE INVENTION

This field of invention is related, but not limited to, the automobile industry. In particular, the field relates to mechanical engines and large-scale mechanical devices that utilize motile lubricating fluids operating in high temperature environments. For these lubricants, it would be beneficial to monitor in real-time the changing fluid properties, the levels of contaminants, and changes in performance to ensure safe and reliable operation of the equipment being protected by the lubricating system. This approach applies to automotive vehicles, aircraft or spacecraft, industrial equipment, wind-turbines, life-saving medical machinery and other critical devices. The conditions of fluids are often detected using a static, periodic approach, typically requiring removing fluid from the system, often by extracting a sample of the fluid to send to testing laboratories around the world, which have established procedures and methods to measure a number of aspects of the lubricating fluid, including historical time-series of various parameters. It is common practice to apply such time-based longitudinal monitoring of the fluid to detect changes over time to gain an understanding of the changes in performance within the closed environment. For example, the presence of specific particles at increasing concentrations can indicate levels of wear and performance of certain underlying components within the system being lubricated. This testing typically measures changes in characteristics of the fluid over time, including detecting changes and deterioration of underlying lubricating fluid and additives and the detection of normal (expected) and abnormal (unexpected) "wear" of the moving parts due to normal operation. Static samples are usually sent to a facility that performs a number of tests, including detecting the presence of foreign materials and objects. In some cases, such as when the lubrication fluid is changed, the lubrication filter is commonly sent as well as the oil for testing and detailed analysis. For both the sample and the filter, this is a destructive "tear down" analysis—such that the filter and the sample are not returned to service, but evaluated and subsequently removed. Tests typically performed in the laboratory include detection of metallic and non-metallic particles, presence of water or other non-lubricant liquids, carbon soot and other components, and in some cases, verification that the underlying chemistry of the lubricant is still intact. A written (or electronic) report is generated and transmitted to the stakeholder upon completion of the testing. Results typically take days or weeks from extraction to stakeholder review.

A number of low-cost lubricating fluid measurement products and techniques are emerging onto the market—including a consumer static "check" of a motor oil sample (see lubricheck.com) which measures the changes in electrical impedance characteristics (electrical capacitance and resistance when a small electrical source is applied across the sensor where a sufficient sample size of the lubricant bridges the sensor electrode across to the detector). This approach performs a single-dimensional measurement of oil sump fluid properties at a point in time in the evolution of the oil (i.e. a static measurement), providing insight only when the operator manually extracts a sample of oil to be tested and only indicates changes in the electrical properties should the data be appropriately logged and tracked over time. This approach has many drawbacks including the interval sampling (only when the operator makes a measurement), as well as the potential for counteracting forces from the presence of multiple contaminants introduced into the fluid to mask the true state/condition of the lubricant. As an example, in the case of an automobile engine, the normal operation of the combustion engine will produce carbon by-products as a result of the operation of the engine (this is what discolors the oil). If a vehicle were producing only this carbon "soot" the resistance would change (increase) due to the introduction of the soot. If at the same time, the engine were undergoing adverse 'wear' to the extent that small metallic particles were produced as an abnormal condition across the internal moving parts, these particles would decrease the resistance, as metal is a better conductor over the base lubricant. In the case where both soot and metallic particles were being produced at the same time, they could partially or completely cancel out some or all the measurable effects—thus providing a false indication of the true condition of the lubricant and underlying engine. A testing laboratory analysis by comparison performs a number of tests which would be able to independently detect the presence of both materials in the base lubricant fluid and provide an accurate report of the condition of the fluid and the resulting system.

Lubricating fluids have to accommodate a wide range of operating conditions—including variances in temperature, pressure, purity, and state change. Lubricants are often optimized for a specific operating environment and temperature range and are expressed in viscosity. Some lubricants are designed to operate with multiple viscosities (e.g., 10 W-30 multi-grade viscosity motor oil). Typically, measurement of the fluid condition and properties is static and performed externally outside this operating environment via sampling when in a static/non-operating state. Static sampling does not necessarily validate the condition of the fluid in the operating state—either within or outside the normal/typical operating range. There are expensive and complex sensors that have been developed for measuring lubricating fluid and other liquids in real time—either for use in laboratory environments and conditions or for very high-value machinery where immediate sensor lubrication information is critical. Companies such as Voelker Sensors, Inc. offer a product for the machine tool industry that measures in real time a number of parameters including oil level, oxidation (change in pH), temperature, etc. The sensor element is not MEMS based and has a larger footprint, and is not suitable in size/form factor for operation within automobile oil/lubrication systems ("*Continuous Oil Condition Monitoring for machine Tool and Industrial Processing Equipment,*" Practicing Oil Analysis (September 2003).

Beyond VSl there have been various implementations of continuous electrical property measurements as performed by Halalay (U.S. Pat. Nos. 7,835,875, 6,922,064, 7,362,110), Freese et. al., (U.S. Pat. No. 5,604,441), Ismail et. al, (U.S. Pat. No. 6,557,396), Steininger (U.S. Pat. No. 4,224,154), Marszalek (U.S. Pat. No. 6,268,737), and others which disclose either a singular vector analysis (electrical) or a time series measurement of electrical properties to derive an understanding of the oil condition. The challenge remains, as in the Lubricheck approach, to overcome the interdependent and true measurement cancelling effects that can report an incorrect oil condition. This is precisely why the fluid testing protocols and laboratories apply tests across multiple dimensions to include spectral analysis as well as tests to determine metal and other foreign object content in the oil samples.

Lubricants are designed to perform beyond their stated range and are further enhanced through the addition of "additives" to extend the lifetime and safety margin of the fluid. Understanding the lubrication longevity is crucial for the safe operation of the system. Replacement of the fluid is performed typically at very conservative (i.e. short) recommended intervals, providing a wide safety margin for the operator. In general, lubricants can operate for significantly longer intervals, or in the case of specific equipment operating in harsh environments (e.g. military equipment used on the battlefield or in mining operations, etc.) may require a more aggressive replacement cycle. It is important to determine when the lubricating fluid cannot continue to perform according to specifications determined by the equipment/system manufacturers. As long as the lubricating fluid is within the safe margin of operation, it may operate indefinitely and not need to be exchanged or replaced with fresh lubricating fluid.

Providing a more precise measure of the fluid's performance can maximize the lifetime of both the lubricant and the equipment the lubricant is protecting. As the cost of the equipment and the hydrocarbon lubricant increase, so does the value of providing both a longer and more precise lifetime of the lubricant and early detection and notification of pending equipment performance deterioration (including motor, filter, and other components in the system, etc.). This approach can potentially save lives when critical equipment failures are detected in advance. In addition, should the fluid fail and contribute to the equipment breaking down, this system potentially eliminates the resources required and time lost to repair/replace the underlying/broken equipment. This approach also avoids the loss of service and resources required to complete oil changes more often than actually needed.

SUMMARY OF THE INVENTION

In embodiments, an integrated system is provided for continuous monitoring of multiple properties of a fluid derived from measurements from a plurality of sensor modalities within a fluid-based closed-system environment. Suitably the system is an in-motor lubrication monitoring system and the monitoring is real-time.

In further embodiments, the systems further comprises engineered nanoparticles, which when bound to target contaminants, provide a unique and measurable signature and can be captured and removed from circulation by a filtration device. Suitably the nanoparticles change state when one or more target environmental conditions are met. In embodiments, the nanoparticles enable the detection of temperature excursions beyond designed operating specifications (i.e., temperatures higher or lower than the operating specification). In further embodiments, the nanoparticles enable the detection of pressure excursions beyond designed operating specifications (i.e., pressures higher or lower than the operating specification). In additional embodiments, the nanoparticles enable the assessment of the performance of said filtration device.

In certain embodiments, the system is built into the form factor of a standard size and shaped oil plug element found within a reciprocating engine oil drain plug, wherein said system is remotely located from a display and processing unit by wired or wireless data telemetry. Suitably the system further comprises a remotely located processing and display unit.

In other embodiments, the sensor modalities comprise at least two of electrical, temperature, magnetic, optical and pressure sensors, suitably at least one of the sensor modalities comprises an inductor. In embodiments, the sensor modalities comprise at least magnetic and optical sensors and in other embodiments the sensor modalities comprise at least electrical, magnetic and optical sensors.

In certain embodiments, the system is contained within an epoxy encapsulation that can support high temperature and high pressure environments contained within the oil plug mechanical design.

In certain embodiments, the system further comprises multiple digital signal processor modules for detection of both single and multiple related fluid characteristics. In embodiments, the systems further comprise multi-stage output signal generation selected from the group consisting of error indication, specific data signature detection signal, specific data signature signal detection strength level, and Fast Fourier Transform (FFT) data output.

In other embodiments, the sensor modality measurements are analyzed using Kalman Filtering techniques, Baysian analytic techniques, hidden-Markov Filtering techniques, fuzzy logic analysis techniques or neural network analysis techniques.

In exemplary embodiments, the sensor modality measurements comprise at least one of the following: differential temperature comparison, differential magnetic sensor comparison, differential inductive sensor comparison, differential electrical impedance comparison, differential optical absorption comparison, any combination and integrated comparison consisting of at least a set of two sensors, data comparison of each sensor vector versus time and temperature, data comparison of an integrated vector consisting of a set of at least two sensors combined, inductive data comparison versus time and temperature, optical data comparison versus time and temperature, optical data comparison versus temperature and pressure, temperature data comparison versus time and pressure to detect peak heat, and other sensor combinations.

Also provided are methods of continuously monitoring an operating fluid of a machine comprising: measuring a first condition of the fluid using a first sensor modality, measuring a second condition of the fluid using a second sensor modality, filtering data from the sensors, integrating the data from the sensors, analyzing the data from the sensors, deriving a property of the fluid from the data, transmitting the derived property of the fluid condition to a receiver, and repeating the process so as to accumulate a time-series of a fluid property that tracks changes in the operating condition of the fluid. In embodiments, the methods further comprise tracking the condition of the fluid by calculating the time series expected rates of change versos observed rates of change of any single or multiple conditions. In additional embodiments, the methods further comprise calculating the expected divergence or convergence across multiple sensor time series data of anticipated and expected measured value changes versus unexpected changes.

Further embodiments, features, and advantages of the embodiments, as well as the structure and operation of the various embodiments, are described in detail below with reference to accompanying drawings.

DETAILED DESCRIPTION OF THE INVENTION

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical valise above and below the stated value by a variance of 20%. It should be understood that use of the term "about" also includes the specifically recited amount.

Technical and scientific terms used herein have the meaning commonly understood by one of skill in the art to which the present application pertains, unless otherwise defined. Reference is made herein to various methodologies and materials known to those of skill in the art.

To provide a more accurate understanding of a fluid, conducting multi-modal tests simultaneously can help to give insight into the true operating status and condition of the lubricating fluid. In embodiments, an integrated system is provided for continuous monitoring of multiple properties of a fluid derived from measurements from a plurality of sensor modalities within a fluid-based closed-system environment. Suitable embodiments utilize a combination of advanced Micro-Electro-Mechanical Systems (MEMS) and semiconductor techniques to place the laboratory tests directly into the fluid to continuously and concurrently measure multiple aspects of the fluid and report these parameters individually to a programmable computer to provide parallel and integrated real-time analysis of the fluid condition. As used herein the term "sensor modalities" include measurement of the magnetic, electrical and optical properties of a fluid as well as measuring the temperature and pressure of the fluid, also called "multi-modal" analysis or tests throughout. These measurements can be done both individually and combined—to provide an integrated insight into the condition and status of the fluid. As single-dimension tests may "obscure" any single result caused by the interplay between two different contaminants in the fluid (e.g. the combination of both electrical resistance increasing and electrical resistance decreasing foreign matter in the system), the application of simultaneous multi-modal sensing using a plurality (i.e., two or more) sensing modalities improves the fidelity and accuracy of the measurements.

To provide an enhanced understanding of the fluid conditions, in embodiments, specially engineered nanoparticles are introduced, designed to enhance sensing and capture of undesired contaminants in the fluid as well as trigger an irreversible property change upon experiencing adverse conditions within the system. Specifically engineered and designed particles are either added to the fluid, or impregnated into the filter and triggered/released into the fluid flow in the presence of contaminants, including water, antifreeze, metal particles, carbon soot, etc. The nanoparticles are not detected until a triggering event. The resulting combined or state-changed particle becomes measurable by the multi-modal sensors (plurality of sensor modalities) and provides a more sensitive and complete understanding of the fluid condition. The resulting combined particle is also better collected by specific filter stages or by magnets (e.g. if paramagnetic) than the contaminant without nanoparticles. This process involves three primary steps: first, the nanoparticles and their surface attachments are designed to activate in the presence of specific contaminant targets, identified through practice and through an understanding of the various contaminant conditions that a lubrication system may encounter. Second, the nanoparticles are introduced into the lubricating system, either as an additive or impregnated into the materials within a filter. Finally, nanoparticles are activated and subsequently detected by the multi-modal sensor system whilst in the operating environment. Further, the combination of the nanoparticles attached to the contaminant suitably becomes better filtered and removed from active circulation within the lubrication system. Alternatively, continued detection and measurement of nanoparticles by the multi-modal sensor may indicate a partial or full failure of the fluid filter.

Nanoparticles can also be released into the fluid during normal operating conditions. In such an embodiment, nanoparticles can be designed to change state if any part of the lubrication system exceeds a target operating condition. For example, such nanoparticles can be designed to change state irreversibly if excessive temperatures are experienced anywhere within the engine lubrication system. The environmentally induced change in nanoparticle properties can later be measured and recognized to indicate that some part of the machinery may be overheating. For example, the surface properties of the nanoparticle can be altered under thermal stress. The changes in surface properties can be recognized by the sensor system, alerting the system of an excessive temperature in a part of the system that otherwise would remain unmeasured. The particles can, for example, be designed to change fluorescence, paramagnetism or other physical or chemical property irreversibly above a target temperature. If any part of the system or component exceeds this design temperature, these particles irreversibly change state. The changed state can be measured at a single point in the system, such as at the multi-dimension sensor. This approach enables a continuous indication of temperature limit at every point in the lubrication system. It provides a benefit equivalent to mounting temperature sensors all over the internal environment, but at much lower complexity using fewer resources.

In embodiments, the engineered nanoparticles themselves serve as lubricating material, as their inherent precursor is based on a carbon nanostructure that has friction-reducing properties. Nanoparticles as well have the inherent property of increasing the surface area/coverage, which improves the sensor detection (e.g. over-temperature condition detection) as well as improve the lubricating coverage within the system. In certain embodiments, the nanoparticles encompass metallic nanoparticles, which are coated with a thin (e.g., about 2 nm) layer of graphitic carbon that allows the covalent chemical functionalization of this carbon to result in chemically functionalized magnetic beads. In other embodiments, the nanoparticles encompass metal magnetic nanoparticles including, for example, cobalt, iron, nickel and alloys. In certain embodiments, the reactive metals are covered by graphene-like carbon layers. In certain embodiments, the inert nature of carbon results in a core-shell magnetic material exhibiting an extremely high thermal and chemical stability. In certain embodiments, the nanobeads can be applied in harsh conditions, such as low pH and high temperatures, without the problem of the oxidation of the metal core. In other embodiments, the nanoparticles include covalent functionalization of the metal nanomagnets. In certain embodiments, the binding relies on carbon-carbon bonds, so no ligands are lost even under demanding process conditions (e.g., high functional loading). The wide range of functionalization allows the preparation of beads with custom surface functionalities. In particular embodiments, the nanoparticles are magnetic beads with covalently functionalized aromatic groups, catalysts and protective groups. The highly magnetic properties allow a high recyclability of the magnetic chemicals for reuse.

In multi-modal sensing, measurements are combined to determine the state (and state changes) tor the fluid using software/firmware programming to compare sensor inputs against reference datum and to detect changing fluid conditions across various measurement dimensions, including time. It is important to set thresholds for detection of foreign contaminants in the oil. For example, a sufficient quantity of water over time can cause corrosion of critical elements normally protected by the lubricating fluid. Based on these thresholds, certain alerts and notices can be provided, either transmitted through an output interface or polled by a wireless interface, optionally using a portable hand-held device, such as a smart phone. To validate the ongoing assessment of the fluid condition, a secondary check can be done to verify the measurements through periodic laboratory sampling. External validation can be part of the conforming calibration process during initial testing of the multi-modal sensors. External validation can also qualify additional lubricating fluids and operating environments. Once the baseline is understood, the thresholds across all the integrated measurements can be programmed into the semiconductor to provide the alerting functionality over and beyond the integrated measurement data outputs.

In additional embodiments, the systems and methods described herein detect use of the wrong fluid or unsuitable lubricating fluid that may be mistakenly introduced into the lubrication system. Operating machinery with the wrong lubricating fluid can cause irreparable harm if not immediately remediated. The multi-modal sensor 'expects' lubricating fluid to be conforming, raising an alert when non-conforming fluid is introduced and subsequently detected.

Specific individual sensors can be combined into a framework that provides a much more complete understanding of the state of the system, both for immediate measurement as well as longitudinal monitoring. Such sensor frameworks greatly improve real-time monitoring of system conditions and greatly improve the ability of the system to automatically recognize and respond to a variety of operational events.

In particular, frameworks incorporating magnetic sensors facilitate the timely recognition of ferrous metal contaminants. Alternatively, such magnetic sensing can detect magnetic nanoparticles. Other sensors in the framework can distinguish between the two. For example, paramagnetic resonance can characterize the nature of the ferrous particles, and potentially their size.

Integrating optical transmissometers, opacity measurements or spectral measurements into the framework provides an indication of particular contaminants, for example, soot, water, or antifreeze solution. Integrated with nanoparticle sensing, detection of contaminants can be enhanced. Further the invention cast be improved through the incorporation of multi-modal sensing analysis to include for example pressure and temperature that may change the optical properties of the fluid. These correcting factors can be applied to improve the accuracy of the measurements.

Integrating electrical measurements into the framework provides a more complete picture of the fluid condition. These measurements can also detect nanoparticles, and can provide independent ways to distinguish between alternative fluid status and condition diagnoses. Nano-particles can be engineered to be activated under specific conditions and circumstances—such as a high temperature incursion—that irreversibly change its state. This state change is detectable by a set of at least one of the sensor modalities.

A control system integrates disparate sensors, utilizing patterns of sensor conditions to "recognize" or "diagnose"

sets of conditions worthy of further attention. Established mathematical algorithms for such analysis include and are not limited to Kalman filtering (and enhanced Kalman filtering), hidden-Markov models, Bayesian analysis, artificial neural networks or fuzzy logic. These control systems can be implemented readily in software, firmware or hardware, or a combination thereof. (See: "*Solutions for MEMS Sensor Fusion*," Esfandyari, J, De Nuccio, R, Xu, G., Solid State Technology, July 2011, p. 18-21; the disclosure of which is incorporated by reference herein in its entirety)

In further embodiments, additional understanding of the fluid properties under different machinery operating conditions can be gained, for example, including "at rest" when the system is not operating, or at "peak heat," which may actually occur after the system shutdown. Temperatures may increase after shutdown when no cooling fluid is circulating. Fluid properties will change as the fluid heats and cools. Measuring these changes across the short heating or cooling interval can yield valuable additional indications and insights into the properties of the lubricating fluid. For example, optical absorption may vary as the fluid heats. In addition, tracking the change in electrical properties with temperature can provide further information as to the condition of the fluid. Deviations may cause the control system to request measurements not only when the machinery is operating but also upon startup or shut down, for example.

The present application overcomes a number of limitations of traditional diagnostics. First, the traditional time delay from fluid sampling to testing may place critical equipment at risk of damage. Sometimes the lubricating fluid is sampled at the time it is being exchanged. While potentially useful for providing insight into the wear of internal parts, machinery may be operated in a potentially unsafe condition until the results are returned from the laboratory. Second, the lubricating fluid may be exposed to extreme temperatures during operating transients, which can be often in excess of 150 degrees C., potentially causing some breakdown of additives in the lubricating fluid. Such problems are not usually detected, as the equipment often is "turned off" during these conditions. Although there is no new heat being generated, residual heat is transferred into the lubricating fluid and can potentially impact its performance. Such temperature extremes often require special engineering effort to design integrated in-situ sensing systems to support reliable operation (e.g. from −50 C to +150 C). Further, sensors and other electrically active elements need to support this environment. Equally important is the support of various pressures that the lubricating fluid may experience during normal and high-load operations. An in-situ sensor framework must be designed to withstand the peak temperatures and pressures experienced within the lubrication system over time.

Several variables provide insight into lubrication fluid properties. Some variables can be measured directly while others can be derived. To achieve a basic understanding of fluid condition, several measurements (sensor modalities) of the lubricant may be helpful, including, for example, temperature, absolute pressure, electrical impedance or resistance, pH, optical transmission or absorption, and magnetic measurements. Measurements are either direct (e.g. temperature via a temperature sensor) or derived—such as degree of carbon buildup via combined measurement of electrical and optical changes. Standard techniques are available and used today such as thermocouples and pressure sensors to acquire some of these data points. Derived measurements (e.g. viscosity conformance within operating range) can be calculated from direct measurements, and can be extrapolated over ranges of temperature and pressure. Additional detection methods include the use of one or more inductive coils and magnetic sensors to enhance detection of moving metallic particles. An optical transmissometer, comprised of an optical light source and optical detector, for example, measures the changes in absorption of optical light at various wavelengths to characterize carbon soot buildup and other potential contaminants and materials in the lubricating fluid. All such measurements should be temperature and pressure compensated (or normalized) to provide an accurate indication of the underlying health of the lubricating fluid.

Viscosity analysis derives a frictional index from multiple sensor readings to determine the net fluidic friction of the lubricant. This invention presents a simple method of deriving viscosity by measuring, for example, two magnetic sensors within the fluidic lubricant in a selected site to measure fluid flow. These magnetic sensors, such as no-latency Hall sensors, are substantially similar and located in close proximity to one another within the lubricant flow. A small turbulence inducer enables measurement near the sensors of slight differences in flow based on induced flow perturbation. This measure can be further integrated with optical absorption measurements using the optical transmissometer. This integrated measure, coupled with temperature or pressure readings, provides a framework for calculating the frictional index. The Hall-based sensors are designed to be as similar as possible. Temporal and spatial variations not caused by the turbulence inducer are subtracted using the two nearly identical sensors. Further, the shape of the turbulence inducer is designed to create subtle changes related to the fluidic velocity, analogous to aeronautical applications in which fluid molecules travel at slightly different speeds above and below an airfoil. Viscosity can be derived from these slight difference measurements along with the local temperature and pressure, using documented lubricant viscosity reference data, providing an indication of real-time lubricant conditions.

Sensors are suitably designed to withstand high temperatures of the engine lubricant. High-temperature thermocouples measure temperature, thick-film resistors enable pressure sensing, and high-temperature magnetic sensors. The optical measuring methods are based on proven high-temperature designs. The optical spectrum suitably ranges from UV to mid-IR in which the lubricating fluid is not emitting energy at high temperature, depending on the fluid and the environment and potential contaminants. The transmissometer range is measured in millimeters and the distance between the emitting element and the receiving element is precisely controlled using known MEMS manufacturing techniques. This distance between the optical emitting and receiving elements must be very accurate. All of these elements have been implemented and operate individually within these extreme temperature and pressure environment in such a manner as to relay useful data. The design is not limited to these methods. At present, these methods are proven effective and provide a simple solution.

In embodiments, the systems and methods described throughout provide real-time monitoring of fluids such as those associated with high-temperature environments present within or associated with internal combustion engines (i.e., monitoring the fluid during engine activity without the delay of removing a sample). Suitably, the systems and methods monitor oil-based fluid lubricants normally used with internal combustion engines, as well as other fluids such as transmission fluids or glycol-based coolants such as anti-freeze, and other fluids in manufacturing environments and critical life-saving medical equipment used in the healthcare industry. The systems and methods suitably provide real-time monitoring using multiple sensor modalities to determine the degradation of the monitored fluid under various operating conditions. Another aspect is the ability of the invention to detect the presence of known harmful particulates, such as metal, within the lubricant. Another aspect addressed is monitoring fluid with a sensor module that is continually submerged within the lubrication fluid. Another aspect addressed is the introduction of specifically engineered nanoparticles that are designed to enhance sensing and capture of contaminants and adverse operating conditions. Another aspect addressed is the parallel and integrated real-time analysis of the fluid condition. This invention also addresses high temperatures and other conditions experienced in the operating environment of such machinery.

Figure 1:
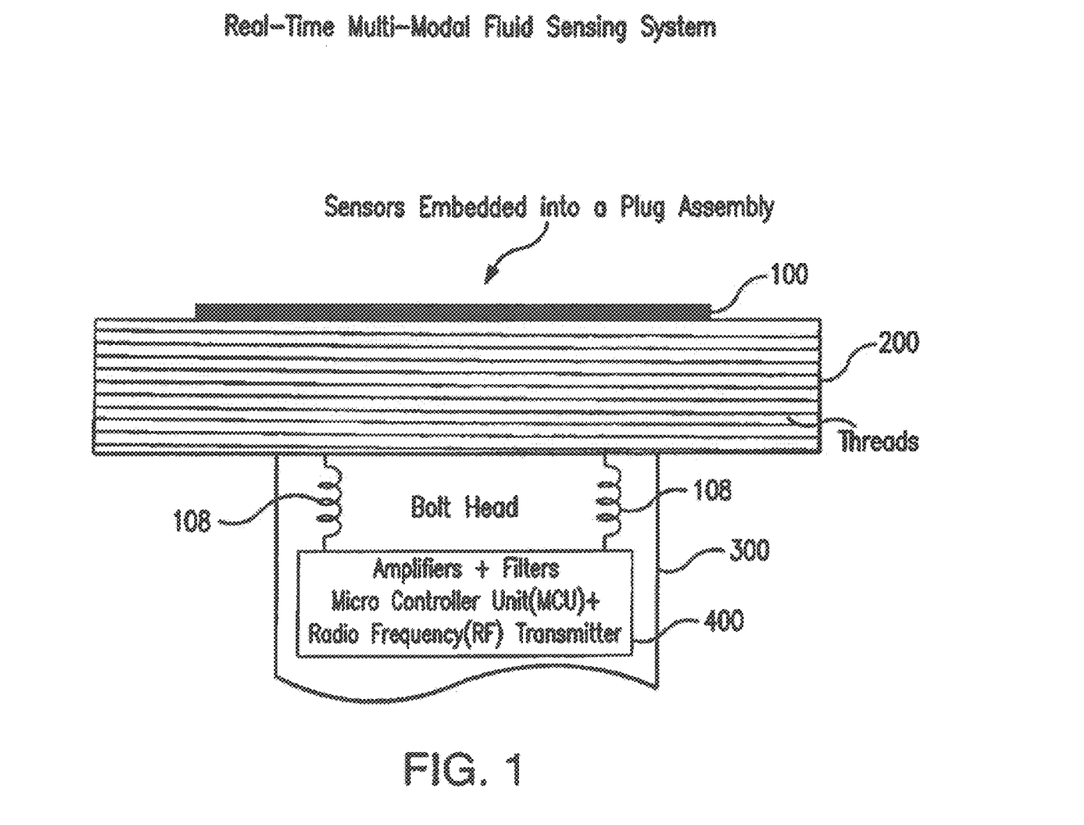
FIG. 1 is a representation of an exemplary real-time multi-modal fluid sensing system described in this application.

In exemplary embodiments a real time multi-modal fluid sensing system is in a self-contained embodiment of a single unit comprising an active sensing environment (100) intended to be submerged in the fluid to be monitored. The sensors are attached to an assembly that can be placed into the fluid with the electronic and active sensors embedded into a plug (300) that is held in place via a threaded bolt (200). The bolt head accommodates the non-sensor elements of the self-contained system (400) to include the microcontroller, filters and other elements. Also suitably contained within the assembly are inductor coils (108) and other methods of signal source to include power to operate the system. The bolt assembly is a self-contained platform that can be installed and removed by a technician. Such an environment is typical of an oil drain plug on an automobile or a similar "low point" in a lubricating return system that may also serve as a reservoir for the fluid. The fluid environment may be subject to changes in temperature and pressure through normal and abnormal operations. As such the sensors are designed to operate within the temperature and pressure specifications—as well as customary tolerances beyond the normal operating environment to be able to detect abnormal conditions.

Figure 2:
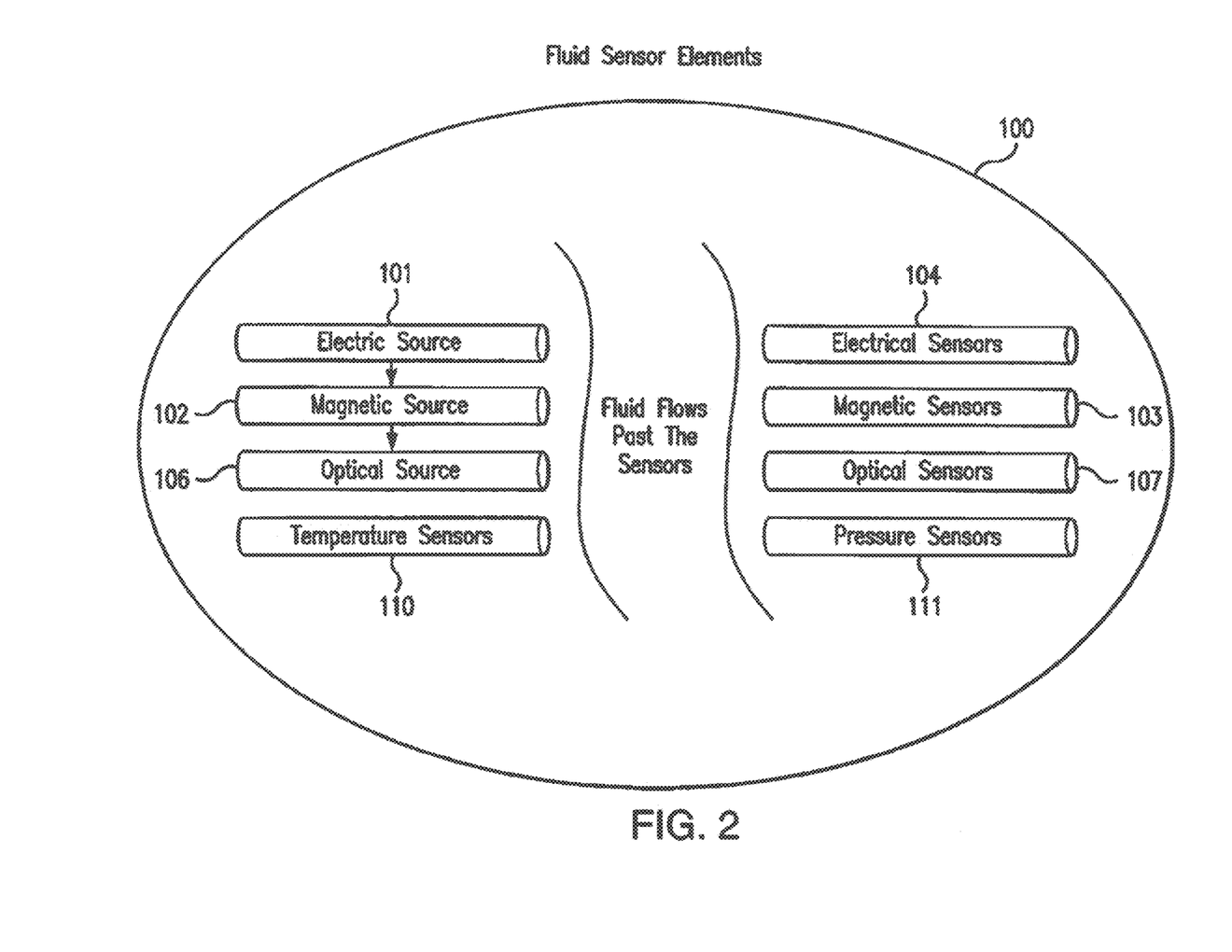
FIG. 2 is a representation of an exemplary major in-engine sensor source and receiving elements making up the multimodal fluid sensor solution.

Within the sensing environment the system programmatically generates its own local and low energy reference signal sources across multiple sensor modalities including magnetic, optical and electrical, and continuously detects values therein as well as passively receives continuous pressure and temperature measurements. The active elements of the sensor platform (100) are intended to be submerged in the fluid under measurement. In the case that the sensor is not submersed, either completely or partially into the fluid, this can be detected and confirmed through multiple sensor confirmation across the optical (106) transmission to optical reception (107) as well as electrical source (101) to reception (104) of expected value tolerances. In this way the condition of lack of fluid can be detected by multiple approaches, as well as verify that both the electrical and optical sensors are correctly and collaboratively cross-checked.

Magnetic sensing is achieved through generating a signal of a pre-defined and programmable characteristic (102) that has a known fixed reference distance within close proximity to the magnetic sensors (103) that is received and processed by a control unit (109) that performs signal amplification, A/D conversion and data filtering. The sensing can be accomplished by one or more sensors (103) of a type such that provide a response rate commensurate with the signal, that can be the same type or different and provide both direct and differential measurements of the fluid condition. The control unit (109) performs the steps to filter and analyze the signals, including amplification, noise reduction filtering which is then communicated to the microcontroller (140). Magnetic measurements when coupled with other measurement dimensions allow for both a confirmation of a detected condition as well as a vector for detection of exception conditions such as a paramagnetic Nano-particle that upon activation develops a magnetic signature that can be detected. The Nano-particle activation is independent of the sensors and is triggered upon an exception condition—such as an extreme temperature limit being exceeded, etc.

Figure 4:
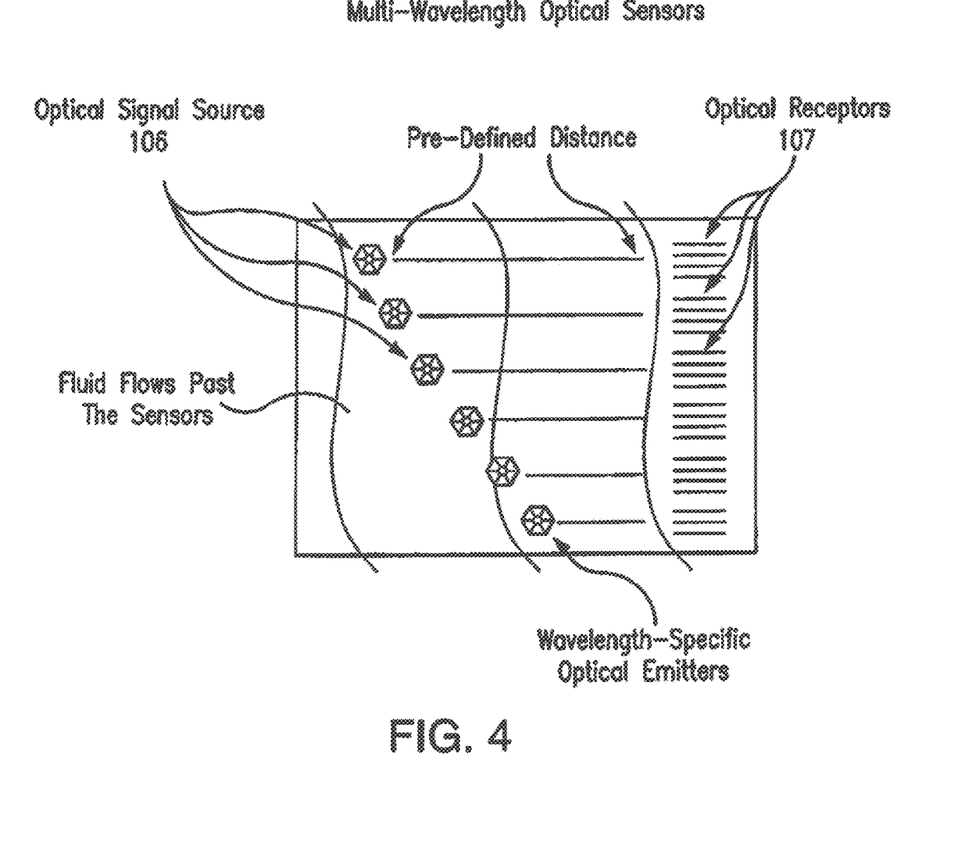
FIG. 4 is an inset diagram of exemplary optical sensors.
Figure 6:
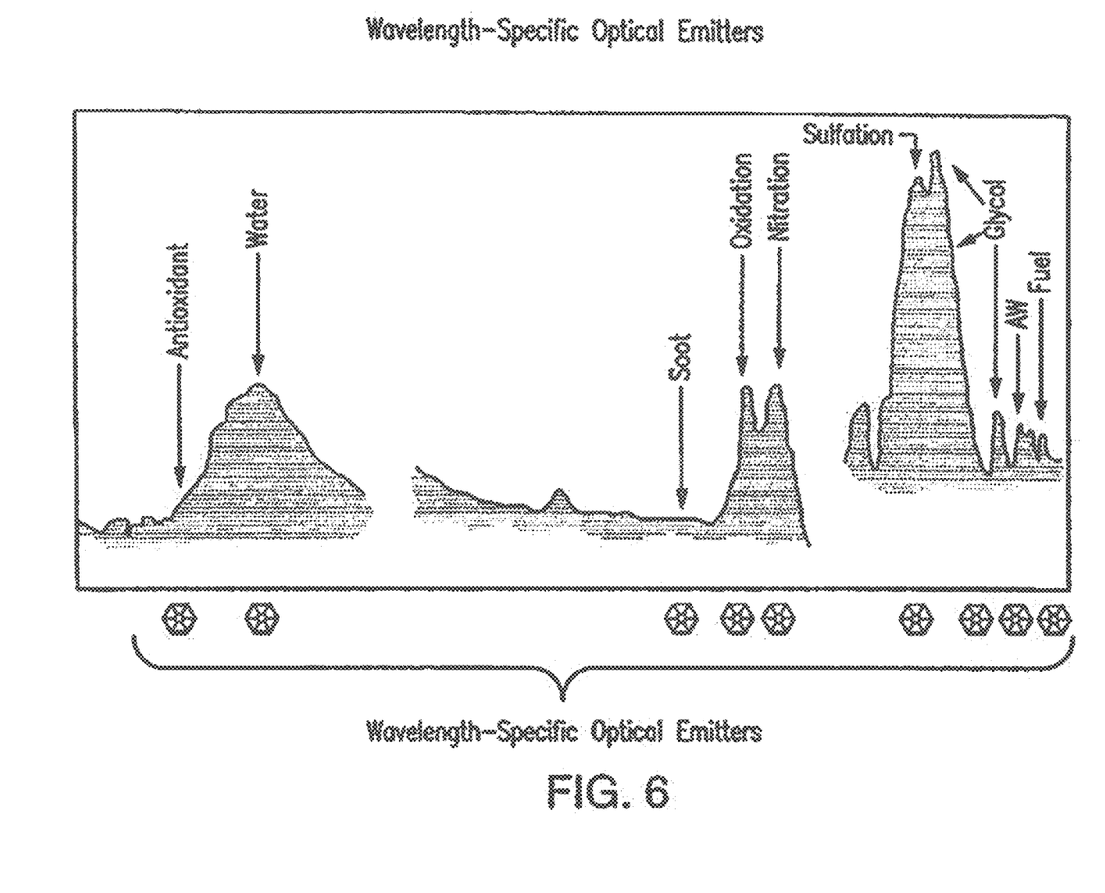
FIG. 6 is a representative framework of discrete wavelengths for the various optical properties detection.

One or more optical sensors (107) can be coupled to one or more optical source(s) (106) which can consist of one or more specific optical wavelength emitters such as narrow frequency tuned light emitting diodes (LEDs) and optical receivers such as photoreceptors. Today's optical emitters can be configured to emit light in narrow frequency bands. Such wavelengths are dependent upon the specific types of fluid and contaminants that may accumulate within the fluid. FIG. 6 shows a representative map over the near infrared region of such. The optical sensing can determine a number of characteristics, including but not limited to the presence of fluid, when the LED is emitting. Further the LEDs can be placed at different known and fixed distances from accompanying photoreceptors to provide a distance based profile of the level of absorption across different frequencies. The embodiment can be accomplished by a single LED emitter to photoreceptors at known distances as well as multiple LEDs spaced at known distances from the photoreceptor pulsed in a known sequence. The controlling logic is managed through software/firmware in the microcontroller (140) and in the pre-processing module (109). Optical sensing can detect the difference in both the specific wavelength absorption and time series changes in optical characteristics. The optical sensing developed operates in both an active and passive mode. In the active mode the optical source pulses light of known strength and wavelengths through the fluid to measure the degree and level of absorption of the light from its source. This small scale transmissometer is configured to detect the specific contaminants and/or changes such as a breakdown in the fluid properties across specific wavelengths, such as shown in FIG. 6. The second mode of operation is to detect optically activated Nano-particles that have been triggered by an exception event such as a temperature excursion. In this mode a signal source (such as, but not limited to, a specific wavelength optical trigger as well as an electrical trigger or magnetic trigger) cause the specifically engineered Nano-particle to fluoresce at a specific frequency that can be subsequently detected by the optical sensors (107). Optical emitters can be pulsed in a programmatic sequence such that a common photoreceptor can be applied as the sensing receiving point and the software in the microcontroller can associate the emitter frequency to the signal response received by the optical photoreceptor sensor. Further, Nano-particle activation is independent from the sensing. The triggering method for the Nano-particle if activated can be independent from an optical trigger, e.g. a Nano-particle can be triggered to fluoresce upon a magnetic or electric field source as its trigger, which is provided by the multi-dimensional sensor.

Sensing changes in the electrical properties is accomplished by an electric source (101) placed at known reference distance from an electric capacitive measuring such as the constant of dielectric of the fluid. The strength and frequency of signal and measurement is based on the programmable microcontroller firmware and is based and dependent on the underlying characteristics of the fluid to be continuously monitored which lies between the source and measurement sensing. The electric resistance and capacitance can be measured across the gap via the data acquisition control unit (109). Different fluids will have different properties, and thus the ability to programmatically configure and control both the source field and sensor receiving properties is an important aspect of this invention. Further, the detection of Nano-particles can be triggered by the introduction of an electrical signal of a certain characteristic such as a frequency, which facilitates detection either by magnetic or optical modalities.

Pressure sensing (111) and temperature sensing (110) are also connected to the data acquisition control unit (109). These sensors can also detect normal and abnormal conditions in heat and pressure levels and provide insight to the operating status of the environment. Fluid condition changes—such as at rest (when the system is not operating) through the peak operating environment—can be evaluated by the programmable microcontroller unit (140). Such applications can be developed in software/firmware to include developing an understanding of both "at rest" and "in operating" conditions. Further, the profile at specific pressures and temperatures can be useful for both determining calculations (offsets due to temperature/pressure—such as if magnetic sensors are based on using the Hail Effect (103)) as well as optical property changes due to temperature and pressure profiles.

Figure 3:
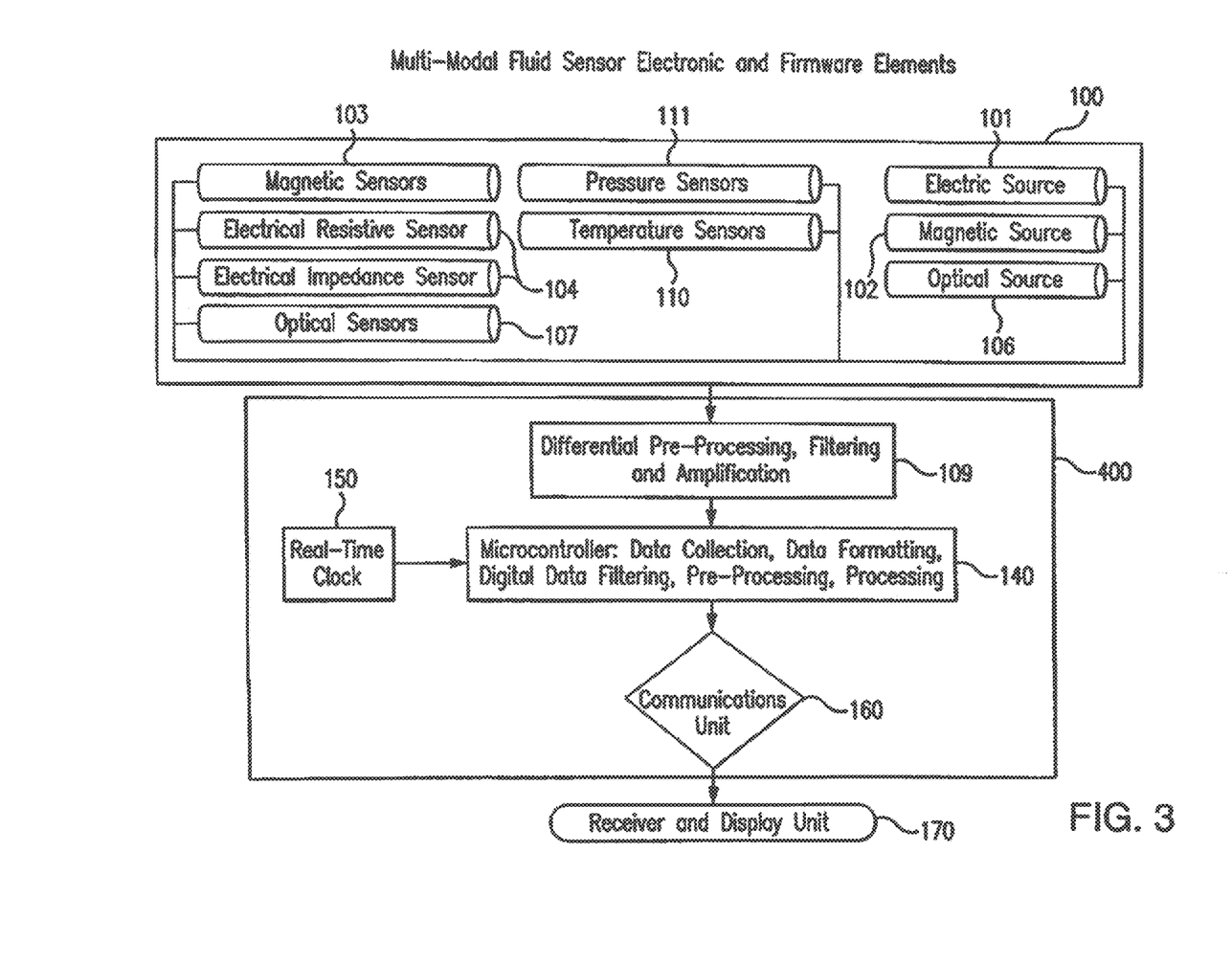
FIG. 3 is a block representation of an exemplary major electronic and firmware elements of the system presented within this application.

A real time clock (150) provides an accurate time basis to trigger monitoring events by the microcontroller module (140) and associate acquired data with a time basis for longitudinal analysis. The real time clock provides both time and date information that can be associated with each of the recorded multi-modal sensor measurements.

The programmable microcontroller (140) also provides both pre and post processing of information including the use of filtering and other algorithms to provide data correction. The results are communicated via a communications module (160) either via a wired or wireless connection to a display unit (170). Both the display unit and the microcontroller may possess internal storage (280) to record and evaluate time-series data.

Figure 5:
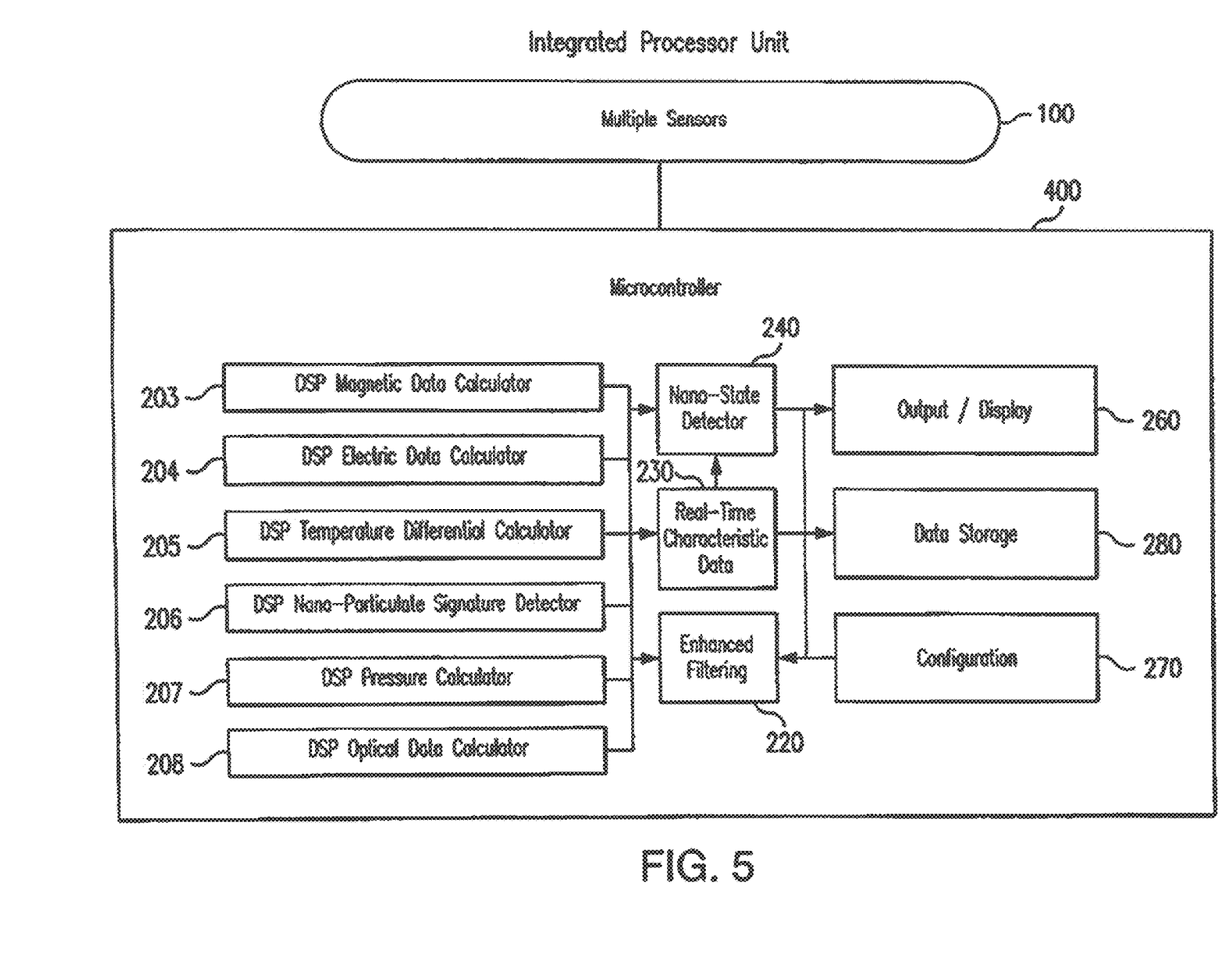
FIG. 5 is a block diagram of exemplary processing electrical and/or firmware elements comprising the Digital Signal Processing modules incorporated within the display and processing portion of the system presented within this application for integrated multi-modal sensor calculations.

Within the microcontroller (140) sensor data is accumulated and subject to additional filtering and integration across the multiple sensors. The raw data is subject to processing by a set of at least one digital signal processor (DSP) for each of the individual sensor modalities such as temperature, pressure, optical absorption, electrical impedance and magnetic signature (203, 204, 205, 206, 207 and 208). A parallel output of the results—both pre and post data correction filtering (220) provides both a raw data output (260) that can be communicated via a communications module (160).

A configuration module (270) can dynamically set filtering and processing parameters to the enhanced filtering (220) to include baseline and error conditions as well as other parameters including configuring storage, event monitoring, triggers, etc. The configuration module is connected via the communications module (160) to an external device.

The Nano-state detector (240) is a continuous check for any triggered and activated Nano-particles that exhibit a signature across a set of at least one of the sensors. This includes the detection of any active signature as profiled and programmed into the microcontroller. The state detector evaluates the outputs of the DSP processing from a set of at least one sensor and integrates real time characteristic (230) data and associated filtering and integrated characteristic data. The Nano-state detector as well provides output to the display (260) and storage (280) as well as can receive configuration parameters via the configuration module (270).

Further, during operation that can be either continuous or polled at intervals as directed by the microprocessor and associated programming software, and further enhanced by the inclusion of a real time clock to provide an accurate time basis (150). Such measurement "cross checking" provides for both inherent value confirmation, improves that data correction (by example Kalman filtering and other algorithmic techniques) and overall sensor system integrity. For many high value systems when a "fault" is detected, often the failure is not in the environment, but the sensor. This invention provides for the cross-correlation and verification of the inherent sensor platform by continuously validating across a number of the measurement criteria such that expected and anticipated sensor output/values can continuously validate the sensor system performance. In this way the isolation of the error condition (e.g. the sensor failure) is in itself a valuable operator insight—to identify and replace a faulty sensor as a known failed device.

The foregoing description, for purpose of explanation, has been described with reference to specific embodiments. The illustrative discussions above, however, are not intended to be exhaustive or to limit the invention to the precise forms disclosed. Many modifications and variations are possible in view of the above teachings. The embodiments were chosen and described in order to explain the principles of the invention and its practical applications, to thereby enable others skilled in the art to best utilize the invention and various embodiments with various modifications as are suited to the particular use contemplated.

What is claimed is:

1. An integrated system for continuous monitoring of multiple properties of a fluid derived from measurements from a plurality of sensor modalities within a fluid-based closed-system environment comprising:
    (a) a bolt comprising an aperture to allow the plurality of sensors to contact said fluid and further comprising a plurality of sensors comprising electrical, magnetic, and optical sensors within a fluid-based closed-system environment, wherein said electrical, magnetic, and optical sensors are embedded within the bolt, and
    (b) a plurality of non-sensor elements comprising a radio frequency transmitter.

2. The system of claim 1, wherein said system is remotely located from a display and processing unit by wired or wireless data telemetry.

3. The integrated system of claim 1, wherein said system is an in-motor lubrication monitoring system.

4. The integrated system of claim 1, wherein said monitoring is real-time.

5. The integrated system of claim 1, built into the form factor of a standard size and shaped oil plug element found within a reciprocating engine oil drain plug, wherein said system is remotely located from a display and processing unit by wired or wireless data telemetry.

6. The integrated system of claim 1, additionally comprising a remotely located processing and display unit.

7. The integrated system of claim 1, wherein the sensor modalities comprise at least two of electrical, temperature, magnetic, optical and pressure sensors.

8. The integrated system of claim 1, wherein at least one of the sensor modalities comprises an inductor.

9. The integrated system of claim 1, wherein the sensor modalities comprise at least magnetic and optical sensors.

10. The integrated system of claim 1, wherein the sensor modalities comprise at least electrical, magnetic and optical sensors.

11. The integrated system of claim 1, contained within an epoxy encapsulation that can support high temperature and high pressure environments.

12. The integrated system of claim 1, further comprising multiple digital signal processor modules for detection of both single and multiple related fluid characteristics.

13. The integrated system of claim 1, further comprising multi-stage output signal generation selected from the group consisting of error indication, specific data signature detection signal, specific data signature signal detection strength level, and Fast Fourier Transform (FFT) data output.

14. The integrated system of claim 1, wherein the sensor modality measurements are analyzed using Kalman Filtering techniques.

15. The integrated system of claim 1, wherein the sensor modality measurements are analyzed using Baysian analytic techniques.

16. The integrated system of claim 1, wherein the sensor modality measurements are analyzed using hidden-Markov Filtering techniques.

17. The integrated system of claim 1, wherein the sensor modality measurements are analyzed using fuzzy logic analysis techniques.

18. The integrated system of claim 1, wherein the sensor modality measurements are analyzed using neural network analysis techniques.

19. The integrated system of claim 1, wherein the sensor modality measurements comprise at least one of the following:
   a) Differential temperature comparison;
   b) Differential magnetic sensor comparison;
   c) Differential inductive sensor comparison;
   d) Differential electrical impedance comparison;
   e) Differential optical absorption comparison;
   f) Any combination and integrated comparison consisting of at least a set of two sensors;
   g) Data comparison of each sensor vector versus time and temperature;
   h) Data comparison of an integrated vector consisting of a set of at least two sensors combined;
   i) inductive data comparison versus time and temperature;
   j) Optical data comparison versus time and temperature;
   k) Optical data comparison versus temperature and pressure;
   l) Temperature data comparison versus time and pressure to detect peak heat; and
   m) Other sensor combinations.

* * * * *